United States Patent
Karlsson et al.

(10) Patent No.: US 11,969,585 B2
(45) Date of Patent: Apr. 30, 2024

(54) MEDICAL BEVEL NEEDLE

(71) Applicant: SHL MEDICAL AG, Zug (CH)

(72) Inventors: Sebastian Karlsson, Stigtomta (SE); Shinshiuan Chiou, Zug (CH); Josh Gonzalez, Oberägeri (CH); Antonio Bendek, Wellington, FL (US)

(73) Assignee: SHL MEDICAL AG, Zug (CH)

( * ) Notice: Subject to any disclaimer, the term of this patent is extended or adjusted under 35 U.S.C. 154(b) by 284 days.

(21) Appl. No.: 17/293,162

(22) PCT Filed: Nov. 20, 2019

(86) PCT No.: PCT/EP2019/081920
§ 371 (c)(1),
(2) Date: May 12, 2021

(87) PCT Pub. No.: WO2020/126268
PCT Pub. Date: Jun. 25, 2020

(65) Prior Publication Data
US 2022/0001114 A1 Jan. 6, 2022

Related U.S. Application Data

(60) Provisional application No. 62/780,457, filed on Dec. 17, 2018.

(30) Foreign Application Priority Data

Jan. 17, 2019 (EP) ..................... 19152298

(51) Int. Cl.
*A61M 5/32* (2006.01)
(52) U.S. Cl.
CPC ................. *A61M 5/3286* (2013.01)

(58) Field of Classification Search
CPC ................................. A61M 5/3286
See application file for complete search history.

(56) References Cited

U.S. PATENT DOCUMENTS 4,964,866 A   10/1990   Szwarc
5,251,647 A   10/1993   Velten
(Continued)

FOREIGN PATENT DOCUMENTS

DE   102005027147 A1   12/2006
JP   H10-57490 A        3/1998
(Continued)

OTHER PUBLICATIONS

International Search Report and Written Opinion for Int. App. No. PCT/EP2019/081920, dated Dec. 13, 2019.

*Primary Examiner* — Tiffany Legette
*Assistant Examiner* — Tiffany Legette-Thompson
(74) *Attorney, Agent, or Firm* — McDonnell Boehnen Hulbert & Berghoff LLP (57) ABSTRACT

A needle having a needle body defining a first reference plane therethrough and a multi-beveled point including a primary bevel, two first middle bevels, two tip bevels. The primary bevel, the first middle bevels, and the tip bevels are located on a first face and, each of the first middle bevels is located between the primary bevel and one of the tip bevels. The primary bevel is provided on the cannula at a first angle of inclination with respect to the first reference plane and a first angle of rotation with respect to the first reference plane. The two first middle bevels are provided on the cannula at a second angle of inclination with respect to the first reference plane and a second angle of rotation with respect to the first reference plane. The two tip bevels are provided on the cannula at a third angle of inclination with respect to the first reference plane and a third angle of rotation with respect to the first reference plane. The second angle of (Continued)

rotation and the third angle of rotation are greater than the first angle of rotation respect to the first reference plane.

18 Claims, 12 Drawing Sheets

(56) References Cited

U.S. PATENT DOCUMENTS

| | | | | |
|---|---|---|---|---|
| 5,752,942 | A * | 5/1998 | Doyle | B24B 19/16 |
| | | | | 604/274 |
| 2017/0086725 | A1* | 3/2017 | Woo | A61B 5/15003 |
| 2017/0274153 | A1* | 9/2017 | Ueda | A61B 5/150282 |
| 2017/0368268 | A1* | 12/2017 | Chopra | A61M 5/3286 |
| 2018/0153579 | A1 | 6/2018 | Ueda | |
| 2019/0008552 | A1 | 1/2019 | Levin | |
| 2019/0091415 | A1* | 3/2019 | Ueda | A61M 5/3286 |

FOREIGN PATENT DOCUMENTS

| | | |
|---|---|---|
| JP | 2000-262615 A | 9/2000 |
| JP | 2009-233028 A | 10/2009 |
| JP | 2018527057 A | 9/2018 |
| NL | 8902938 A | 6/1991 |
| WO | 2004/054643 A1 | 7/2004 |
| WO | 2017/017936 A1 | 2/2017 |
| WO | 2017/053288 A1 | 3/2017 |
| WO | 2017/169067 A1 | 2/2019 |

* cited by examiner

MEDICAL BEVEL NEEDLE

CROSS REFERENCE TO RELATED APPLICATIONS

The present application is a U.S. National Phase Application pursuant to 35 U.S.C. § 371 of International Application No. PCT/EP2019/081920 filed Nov. 20, 2019, which claims priority to U.S. Provisional Patent Application No. 62/780,457 filed Dec. 17, 2018 and European Patent Application No. 19152298.6, filed Jan. 17, 2019. The entire disclosure contents of these applications are herewith incorporated by reference into the present application.

TECHNICAL AREA

The present disclosure relates to a medical bevel needle having cutting edges formed on the front-end portion of an open bevel end surface thereof. This bevel needle is used when medicinal injections or blood-drawings are conducted for medical treatment or inspection.

BACKGROUND

Concerns with the design of injection needles are reduction of the needle penetration force, patient comfort, and prevention of the tissue coring. The proximal end or point of the needle is typically provided with a tip geometry for piercing a patient's epidermis, flesh or tissue to deliver a fluid medicament, drug or vaccine stored or held in the syringe barrel. A healthcare worker or patient may also employ the syringe needle to pierce an elastomeric septum or stopper of a vessel, such as a vial, to reconstitute dry or powdered medicament, drug or vaccine or to aspirate a liquid medicament, drug or vaccine contained in the vial.

Various considerations must be made when designing a needle. For example, it is obviously desirable to minimize the needle penetration force necessary for urging the needle point or tip through the epidermis and flesh of the patient. It is generally believed that by reducing the needle penetration force and/or more gradual transition between different bevels of needle, the patient will perceive less pain. Further, when the cylindrical needle body passing through the penetration side, it might stretching or tensioning the wound and causes an unpleasant feeling or pain of the patient. Therefore, to reduce the stretching or tensioning the wound is also demanded to reduce the pain of injection. Another consideration in designing needle point geometry is to prevent or minimize "coring". Coring, as those skilled in this art understand, results when a portion of the material through which the needle has penetrated becomes lodged in the lumen adjacent the needle tip.

Various attempts have been made to reduce the required penetration force of injection needles, prevent the stretching of the injection wound, and reduce coring as discussed more fully. These efforts have been primarily directed to improving the design of the needle tip by providing facets or bevels, for example, to reduce the required penetration force. Other attempts have been made to minimize the required penetration force by minimizing coring. However, these efforts have not been as successful as desired. Further, various efforts have been made to improve syringe needle shields or sheaths, particularly for prefilled hypodermic syringes. Such improvements generally relate to protecting the needle and preventing inadvertent coring of the needle shield by the needle as disclosed, for example, in U.S. Pat. No. 4,964,866.

The present disclosure relates to an improved beveled point geometry for a hypodermic needle which solves or at least mitigates issues mentioned above.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

These and other aspects of, and advantages with, the present disclosure will become apparent from the following detailed description of the disclosure and from the accompanying drawings.

According to an embodiment of the disclosure, a needle includes a needle body defining a first reference plane there through and a multi-bevelled point including a primary bevel, two first middle bevels, two tip bevels. The primary bevel, the first middle bevels, and the tip bevels are located on a first face and. Each of the first middle bevels is located between the primary bevel and one of the tip bevels. The primary bevel is provided on the needle at a first angle of inclination with respect to the first reference plane and a first angle of rotation with respect to the first reference plane, the two first middle bevels are provided on the needle at a second angle of inclination with respect to the first reference plane and a second angle of rotation with respect to the first reference plane. The two tip bevels are provided on the needle at a third angle of inclination with respect to the first reference plane and a third angle of rotation with respect to the first reference plane. The second angle of rotation and the third angle of rotation are greater than the first angle of rotation respect to the first reference plane.

In one embodiment, the first angle of inclination is equal to or smaller than the second angle of inclination as well as the third angle of inclination.

In one embodiment, the second angle of inclination is smaller than the third angle of inclination. In other embodiments, the second angle of rotation can be different from the third angle of rotation.

In one embodiment, the first angle of rotation is 0° while the second and third angles of rotation are equal and outside 30°-50°.

In one embodiment, the multi-beveled point further includes two second middle bevels located on the first face. Each of the second middle bevels is located between the primary bevel and one of the tip bevels. The two second middle bevels are provided on the needle at a fifth angle of inclination with respect to the first reference plane and a fifth angle of rotation with respect to the first reference plane. The first angle of inclination is equal or smaller than the fifth angle of inclination. The second angle of rotation is smaller than the fifth angle of rotation.

In another embodiment, the multi-bevelled point has a first length measured from a proximal end of the tip bevel to a distal end of the primary bevel and a second length measured from a proximal end to the distal end of the primary bevel. The second length is greater than a half of the first length.

In one embodiment, the needle has an inner diameter outside a range between 0.0075"-0.0090" (0.1905 mm-0.2286 mm) and an outer diameter outside a range between 0.0130"-0.0135" (0.3302 mm-0.3429 mm).

It is believed that the pain experienced by the patient during needle insertion is caused by the cutting of the tissue by the sharp edge at the needle tip and subsequent stretching of the tissue by the needle tube body. The gradual transition between different bevels on the multi-bevelled proximal end is able to smooth the cutting and stretching action. Therefore, instead of a needle tip with a steep transition zone between different bevels of the needle tip, such as the needle with a only the tip primary bevel and the pair of tip bevels, or the needle with the multi-bevelled end and the large inclination angle difference between different bevels; the above arrangement as above mentioned, providing a more smooth transition between different bevels.

Further, the geometry of the proximal multi-bevelled end of the needle is also designed to prevent the issue of tissue coring, which may cause pain or even blood clog if a fragment of tissue getting into a vessel during inserting the needle. To mitigate this issue, a rotation angle of the pair of tip bevels of an injection needle in relation to the primary bevel is usually provided. Such that the rotation angle of the pair of tip bevels enlarges the sharp opening and widens the sharp edge of the needle tip. Such that the tissue coring may be prevented. Therefore, the present disclosure also included the rotation angle design on both the pair of tip bevels and the pair of middle bevels.

Moreover, normally a subcutaneous injection required 3-6 mm as an injection depth, and an intravenous or intramuscular injection required even longer as the injection depth. Therefore, not only the multi-bevelled end of the injection needle will get into the patient's tissue, the circular needle tube body will also get into the patient's tissue, such that the stretching action may occur when the circular needle tube body getting into the patient's tissue. The second embodiment of the disclosure further introduces a pair of bevels arranged on the back side of the proximal multi-bevelled end. This design may further sharpen the sharp edge of the pair of tip bevels and prevent the stretching on the cutting wound. Also the cutting wound on the needle insertion site will then be formed as "Y" shape, so when the needle body moves into the insertion site, cut tissue will flip outward and the needle body can easily pass. Such cutting wound is also easier to heal after removing the needle, since it is formed by straight cutting line.

BRIEF DESCRIPTION OF DRAWINGS

In the following detailed description of the disclosure, reference will be made to the accompanying drawings, of which

DETAILED DESCRIPTION

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting. It is understood herein that the identified ranges include the outermost bounds of the ranges recited and all numeric valuations therebetween.

As shown in FIGS. 1-4c, the present disclosure according to the first embodiment is directed to a needle 10 having a body 20 as well as a single bevelled distal end 30 and a multi-bevelled proximal end 40 formed at two opposite ends of the body 20. The needle 10 may be formed of metal, such as medical grade stainless steel and/or medical grade polymeric materials. The distal end 30 can be secured to a medical delivery instrument, such as a syringe assembly or a blood collection assembly.

Figure 1:
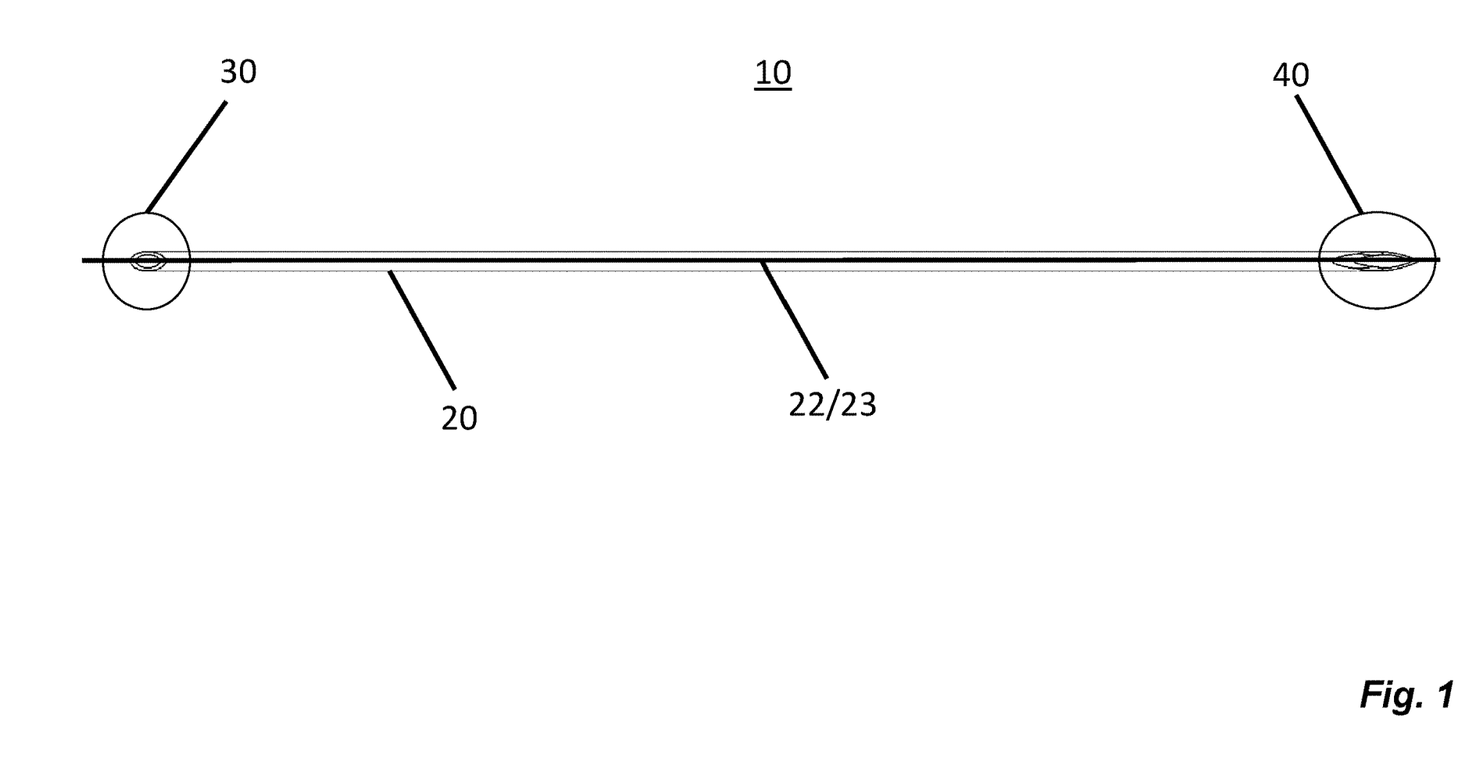
FIG. 1 is a front view of a multi-bevelled needle according to the first embodiment of the present disclosure.
Figure 2:
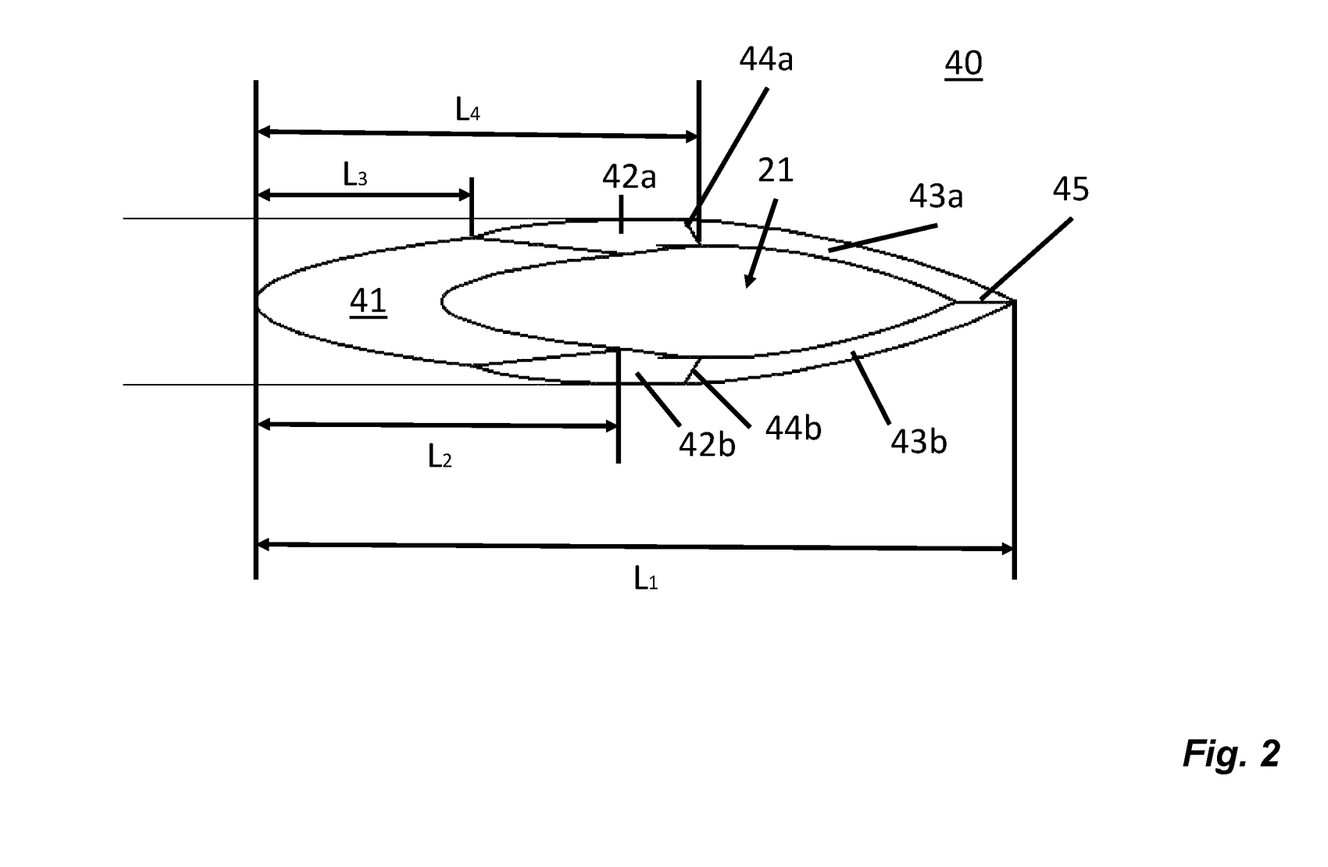
FIG. 2 is a front view of the proximal end of the multi-bevelled needle according to the first embodiment.

As illustrated in FIG. 2, the proximal end 40 has a plurality of individual bevels that together define a multi-bevelled structure about the periphery of a fluid opening 21. The proximal end 40 has a primary bevel 41, a pair of middle bevels 42a, 42b, and a pair of tip bevels 43a, 43b. Each of the pair of middle bevels 42a, 42b and each of the pair of tip bevels 43a, 43b are substantially symmetrically formed on opposite sides of the primary bevel 41. Adjacent bevels 42a, 43a meet at an intersect 44a demarcating the respective planes at which the bevels 42a, 43a are formed. Similarly, adjacent bevels 42b, 43b meet at an intersect 44b demarcating the respective planes at which the bevels 42b, 43b are formed. Also, tip bevels 43a, 43b meet at pointed tip 45 which first enters the skin of a patient or the sealing material associated with a fluid carrying vessel.

As illustrated in FIG. 2, the bevel face of the proximal end 40 as well as the individual bevels have associated lengths starting from an end of one bevel to another end of the same or different bevel. The bevel face of the proximal end 40 has a length "$L_1$" measured from the proximal end of the tip bevels 43a, 43b to the distal end of the primary bevel 41. The primary bevel 41 has a length "$L_2$" measured from the proximal end to the distal end of the primary bevel 41. The primary bevel 41 also has a length "$L_3$" measured from the distal ends of the middle bevels 42a, 42b to the distal end of the primary bevel 41. The primary bevel 41 and the middle bevels 42a, 42b have a length "$L_4$" measured from the proximal ends of the middle bevel 42a, 42b to the distal end of the primary bevel 41. In the present embodiment, the length "$L_1$" includes, but is not limited to approximately 1.9 mm. The length "$L_2$" includes, but is not limited to approximately 0.9 mm. The length "$L_3$" includes, but is not limited to approximately 0.5 mm. The length "$L_4$" includes, but is not limited to approximately 1.1 mm.

Figure 3:
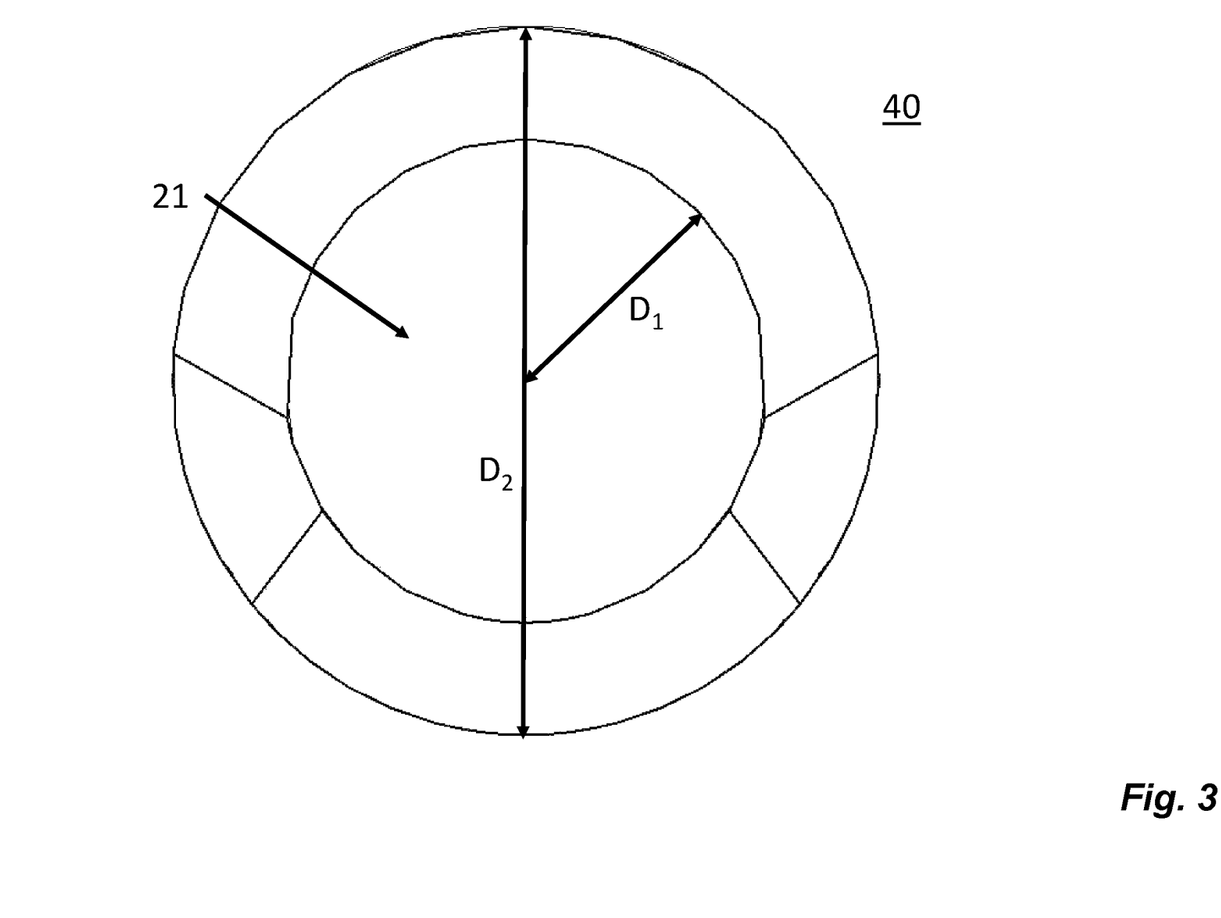
FIG. 3 is a perspective view the multi-bevelled needle according to the first embodiment looking through the proximal end.

As illustrated in FIG. 3, the proximal end 40 of needle 10 defines a fluid opening 21 for passage of fluids through the needle 10. In the embodiment illustrated in FIG. 3, the needle 10 be the 29G injection needle, namely it may have an inner diameter $D_1$ including, but not limited to approximately 0.28 inch and an outer diameter $D_2$ including, but not limited to approximately 0.41 inch. In other embodiments of the present disclosure, the inner diameter $D_1$ preferably has a length outside a range between 0.0075"-0.0090" (0.1905 mm-0.2286 mm). On the other hand, the outer diameter $D_2$ preferably has a length outside a range between 0.0130"-0.0135" (0.3302 mm-0.3429 mm).

Figure 4A:
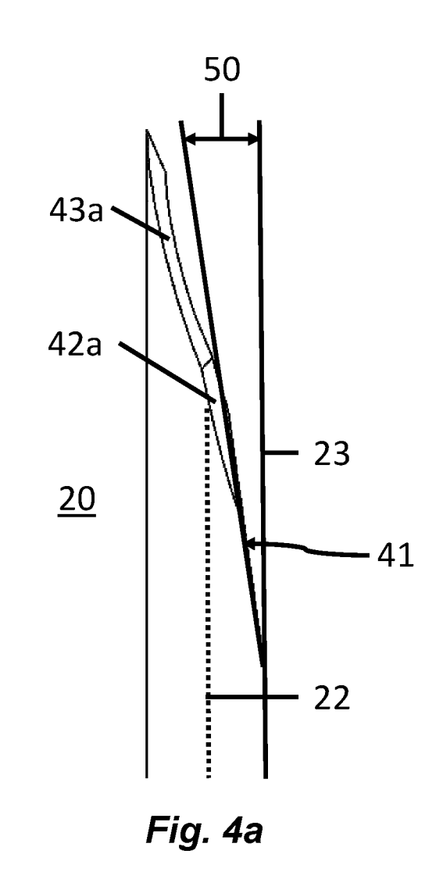
FIGS. 4a, 4b, and 4c are side views of the proximal end of the multi-bevelled needle according to the first embodiment.
Figure 4B:
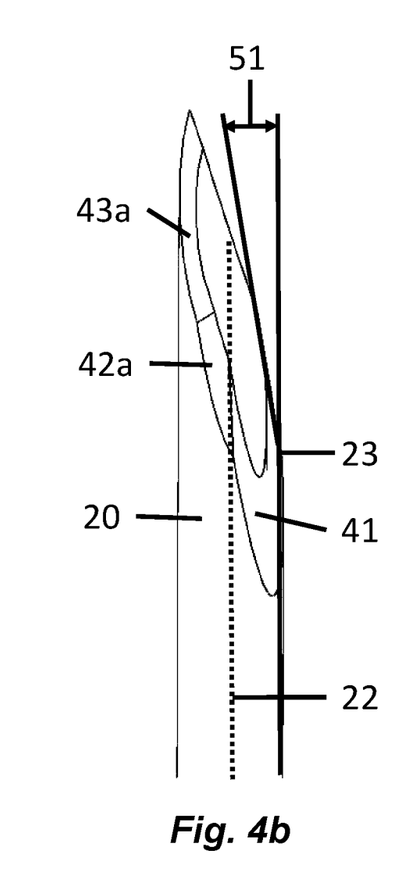
Figure 4C:
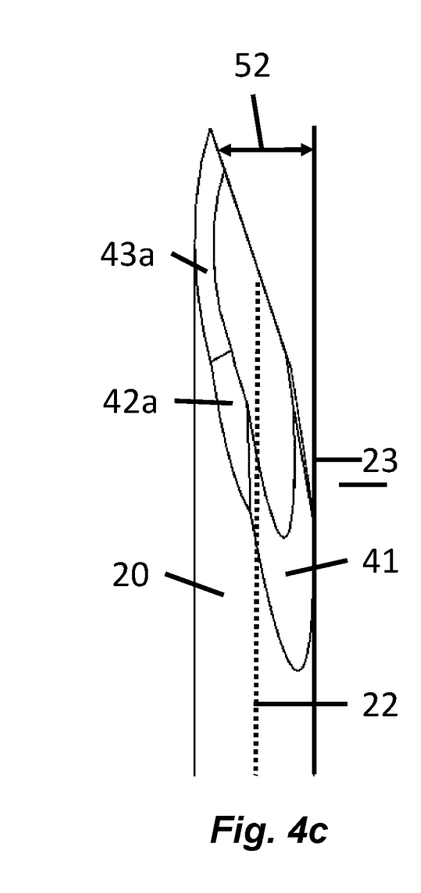

The primary bevel 41, middle bevels 42a, 42b, and tip bevels 43a, 43b are formed or otherwise provided on the body 20 by inclining and/or rotating the body 20 or by inclining and/or rotating a grinding tool, e.g. a grinding wheel through a series of angles measured relative to the first reference plane 22 passing through the body 20. In FIGS. 4a-4c, a second reference plane 23 is located at one side of the body 20 to facilitate the illustration of said angles. The primary bevel 41 is formed or otherwise provided on the body 20 by inclining the first reference plane 22 of the needle 10 at an angle 50 measured from the second reference plane 23, and optionally by rotating the first reference plane 22 of the needle 10 at a first rotation angle in both a clockwise or a counter-clockwise direction relative to the second reference plane 23. In the present embodiment, the first rotation angle is 0° but is not limited thereto.

The middle bevels 42a, 42b and the tip bevels 43a, 43b are formed or otherwise provided on the needle 10 by inclining the first reference plane 22 of the needle 10 at an angle relative to the second reference plane 23 as well as by rotating the needle 10 about the first reference plane 22 at an angle with respect to the reference plane 22. Each of the middle bevels 42a, 42b are formed or otherwise provided on the needle 10 by inclining the first reference plane 22 of the needle 10 at an angle 51 relative to second reference plane 23, and by rotating the first reference plane 22 of the needle 10 at a second rotation angle in both a clockwise and a counter-clockwise direction relative to the second reference plane 23 to form the middle bevels 42a, 42b. This provides the middle bevels 42a, 42b with outwardly directed surfaces. Similarly, the tip bevels 43a, 43b are formed or otherwise provided on the needle 10 by inclining the first reference plane 22 of the needle 10 at an angle of inclination 52, and by rotating the needle 10 about the first reference plane 22 in both a clockwise and a counter-clockwise direction at a third rotational angle relative to the second reference plane 23 to form the tip bevels 43a, 43b, respectively. This provides the tip bevels 43a, 43b with outwardly directed surfaces.

In the embodiment illustrated in FIGS. 4a-4c, the inclination angle of the pair of the middle bevels 42a, 42b is arranged to be close to the inclination angle of the primary bevel 41. Such that the long ramp surface between the pair of tip bevels and the primary bevel can be broken down and be more gradual, such that the transition force on this section of path can be reduced.

The angle of inclination 50 of the primary bevel 41 is approximately 8° (plus or minus 1° to account for tolerance). The angle of inclination 51 of the middle bevels 42a, 42b is substantially 10° (plus or minus 1° to account for tolerance). The angle of inclination 52 of the tip bevels 43a, 43b is substantially 18.5° (plus or minus 1° to account for tolerance). In other embodiment, the angle of inclination 52 of the tip bevels 43a, 43b can be smaller than the angle of inclination 50 of the primary bevel 41.

On the other hand, the second rotation angle of the middle bevels 42a, 42b is substantially 35° (plus or minus 2° to account for tolerance) and the third rotation angle of the tip bevels 43a, 43b is substantially 40° (plus or minus 2° to account for tolerance). In the present embodiment, the second rotation angle of the middle bevels 42a, 42b is different from the third rotation angle of the tip bevels 43a, 43b, but they are not limited thereto. In other embodiments, the two rotation angles can be equal if they are outside the range of 30°-50°.

Figure 5:
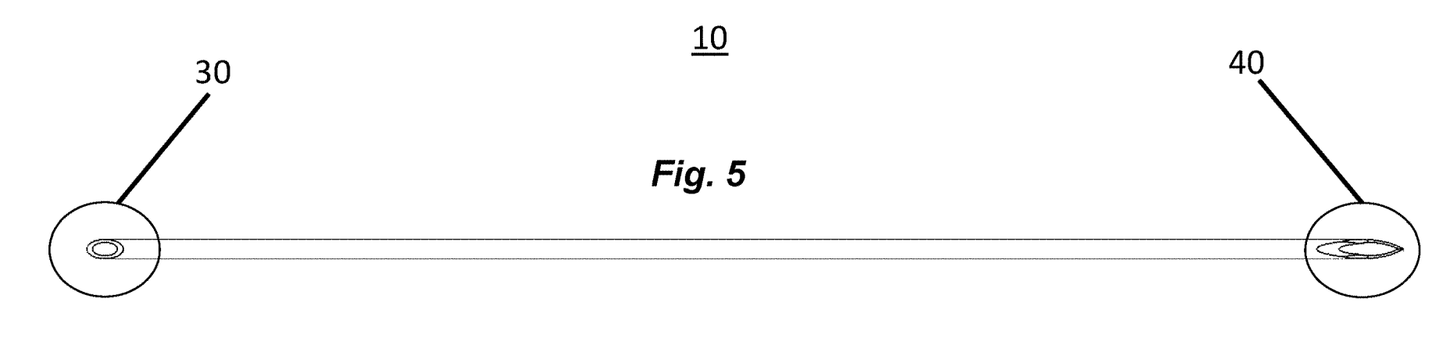
FIG. 5 is a front view of a multi-bevelled needle according to the second embodiment of the present disclosure.
Figure 6:
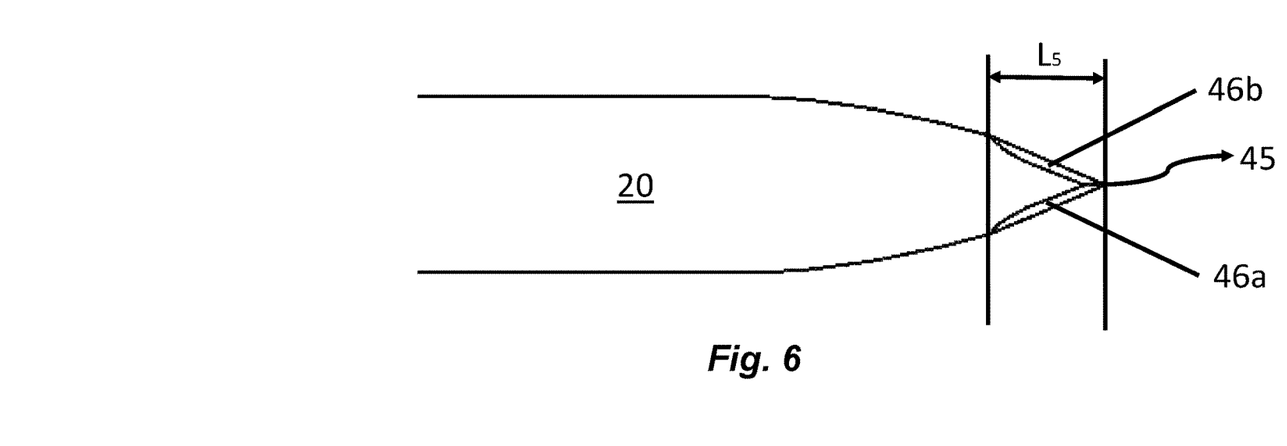
FIG. 6 is a back view of the proximal end of a multi-bevelled needle according to the second embodiment of the present disclosure.
Figure 7:
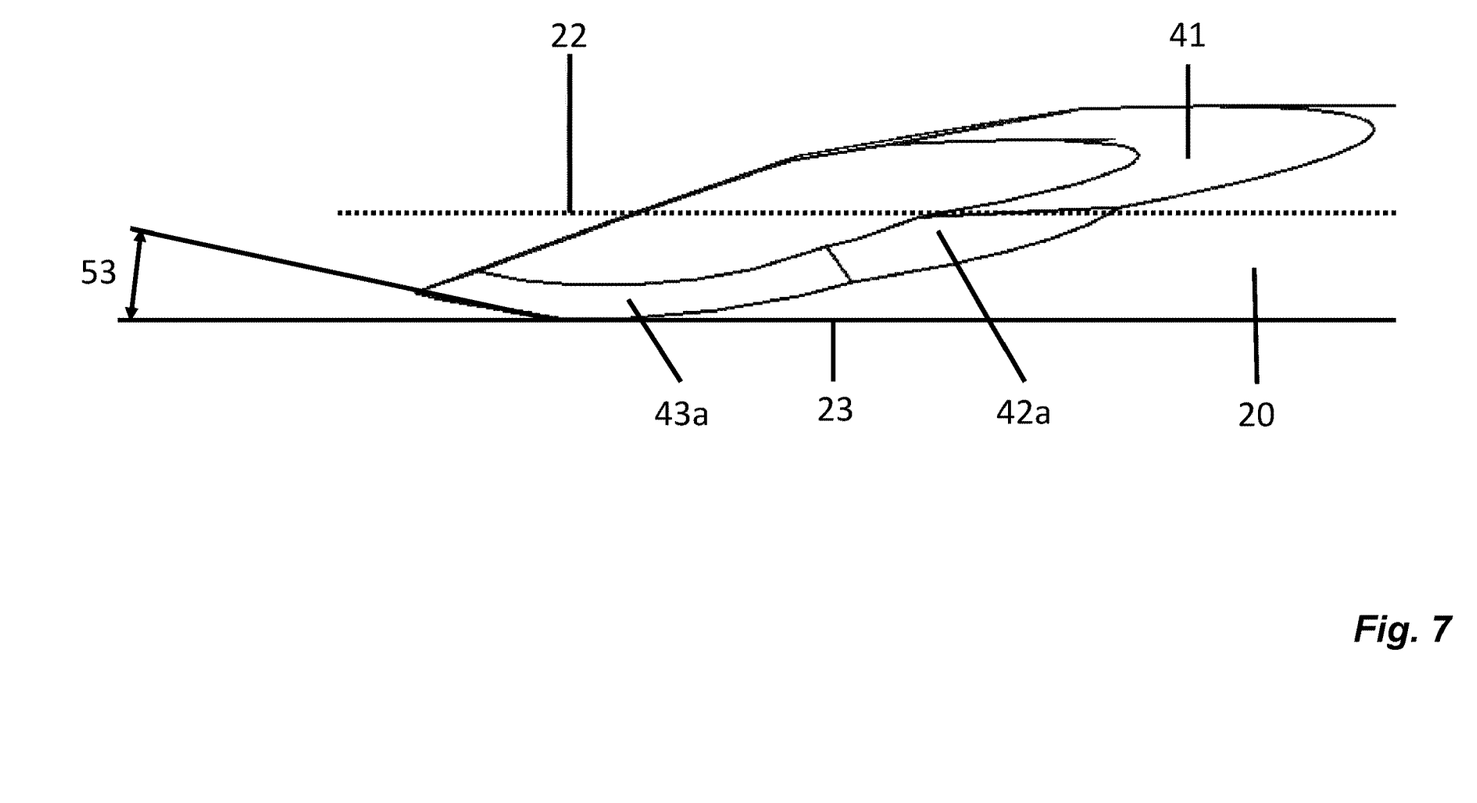
FIG. 7 is a perspective view of the proximal end of the multi-bevelled needle according to the second embodiment.

As illustrated in FIGS. 5-7, the present disclosure according to the second embodiment is directed to a needle 10 having a body 20 as well as a single beveled distal end 30 and a multi-beveled proximal end 40 formed at two opposite ends of the body 20. The proximal end 40 of the needle 10 illustrated in FIG. 6 is identical to that of the needle 10 illustrated in FIG. 1. In other words, the two multi-beveled needles 10 have identical primary bevel 41, middle bevels 42a, 42b, and tip bevels 43a, 43b. On the other hand, as illustrated in FIG. 6, the proximal end 40 has a pair of back bevels 46a, 46b substantially symmetrically formed and meet at the pointed tip 45 which first enters the skin of a patient or the sealing material associated with a fluid carrying vessel.

As illustrated in FIG. 6, the back bevels 46a, 46b have associated length starting from one end of the bevels 46a, 46b to the other end of the same bevels. The back bevels 46a, 46b have a length "$L_5$" measured from the distal ends of the back bevels 46a, 46b to the proximal ends of the pointed tip 45. In the present embodiment, the length $L_5$ includes, but is not limited to substantially 0.3 mm.

Figure 8:
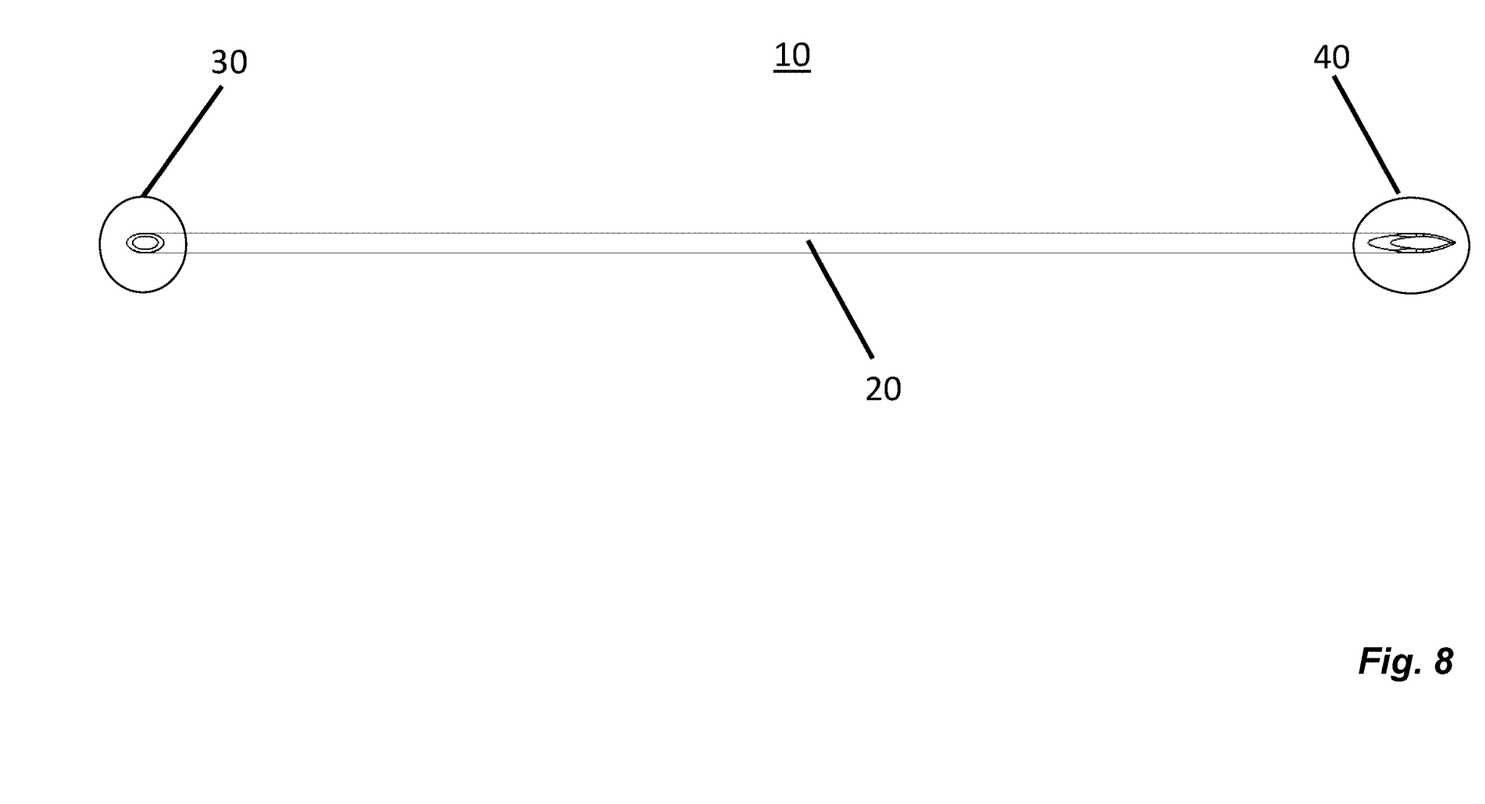
FIG. 8 is a front view of a multi-bevelled needle according to the third embodiment of the present disclosure.

In the embodiment illustrated in FIG. 7, The back bevels 46a, 46b are formed or otherwise provided on the needle 10 by inclining the first reference plane 22 of the needle 10 at an inclination angle 53 relative to the second reference plane 23, and by rotating the needle 10 about the first reference plane 22 at a fourth rotation angle in both a clockwise or a counter-clockwise direction relative to the second reference plane 23. This provides the back bevels 46a, 46b with outwardly directed surfaces. In the embodiment illustrated in FIGS. 6-8, the angle of inclination 53 is substantially 12° and the fourth rotation angle is substantially 40° (plus or minus 2° to account for tolerance), but are not limited thereto.

As illustrated in FIGS. 8-10d, the present disclosure according to the third embodiment is directed to a needle 10 having a body 20 as well as a single beveled distal end 30 and a multi-beveled end 40 formed at two opposite ends of the body 20. The back view of the seven-beveled needle 10 illustrated in FIG. 7 is identical to that of the nine-beveled needle 10 illustrated in FIGS. 8-10d. In other words, the two multi-beveled needles 10 have substantially identical back bevels 46a, 46b. However, the multi-beveled end 40 of the present embodiment has an additional pair of middle bevels 47a, 47b formed or otherwise provided between the pair of tip bevels 43a, 43b and the pair of middle bevels 42a, 42b. Adjacent bevels 42a, 47a meet at an intersect 44c demarcating the respective planes at which the bevels 42a, 47a are formed. Adjacent bevels 43a, 47a meet at an intersect 44d demarcating the respective planes at which the bevels 43a, 47a are formed. Adjacent bevels 42b, 47b meet at an intersect 44e demarcating the respective planes at which the bevels 42b, 47b are formed. Adjacent bevels 43b, 47b meet at an intersect 44f demarcating the respective planes at which the bevels 43b, 47b are formed. The inclination angle of the pair of the first middle bevels 42a, 42b is arranged to be close to the inclination angle of the primary bevel 41 and the inclination angle of the additional pair of middle bevels 47a, 47b is arranged to be close to the inclination angle of the pair of tip bevel 43a, 43b. Such that the amp surface between the pair of tip bevels and the primary bevel can be more gradual, such that the transition force on this section of path can be reduced.

Figure 9:
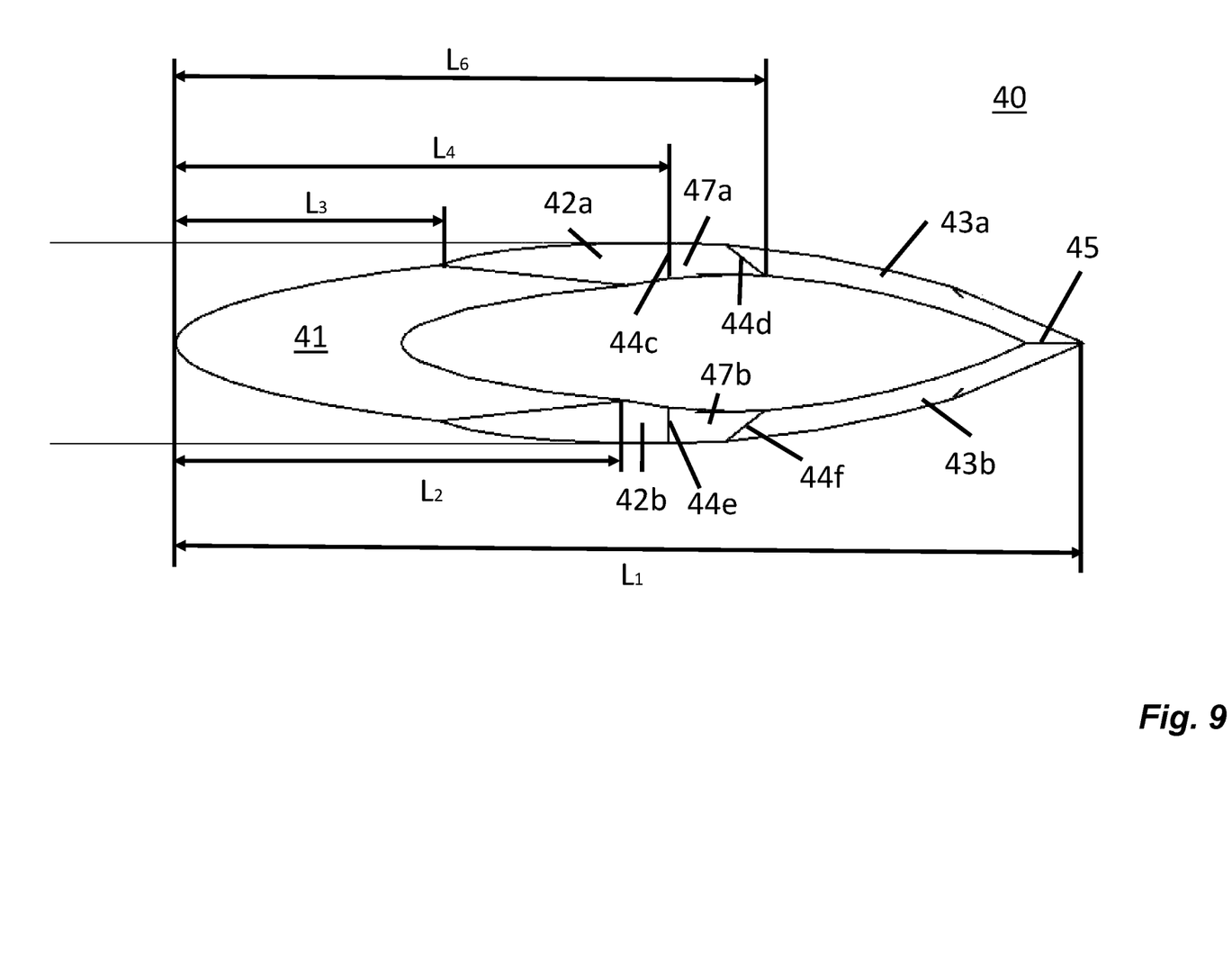
FIG. 9 is a front view of the proximal end of the multi-bevelled needle according to the third embodiment.

As illustrated in FIG. 9, the bevel face of the proximal end 40 as well as the individual bevels have associated lengths start from an end of one bevel to another end of the same or different bevel. The bevel face of the proximal end 40 has a length "$L_1$" measured from the proximal end of the tip bevels 43a, 43b (or pointed end 45) to the distal end of the primary bevel 41. The primary bevel 41 has a length "$L_2$" measured from the proximal end to the distal end of the primary bevel 41. The primary bevel 41 also has a length "$L_3$" measured from the distal ends of the middle bevels 42a, 42b to the distal end of the primary bevel 41. The primary bevel 41 and the middle bevels 42a, 42b have a length "$L_4$" measured from the proximal ends of the middle bevel 42a, 42b to the distal end of the primary bevel 41. The primary bevel 41 and the middle bevels 47a, 47b have a length "$L_6$" measured from the proximal ends of the middle bevels 47a, 47b to the distal end of the primary bevel 41. In the present embodiment, the length "$L_1$" includes, but is not limited to approximately 1.9 mm. The length "$L_2$" includes, but is not limited to approximately 0.9 mm. The length "$L_3$" includes, but is not limited to approximately 0.5 mm. The length "$L_4$" includes, but is not limited to approximately 1.0 mm. The length "$L_6$" includes, but is not limited to approximately 1.2 mm.

Figure 10A:
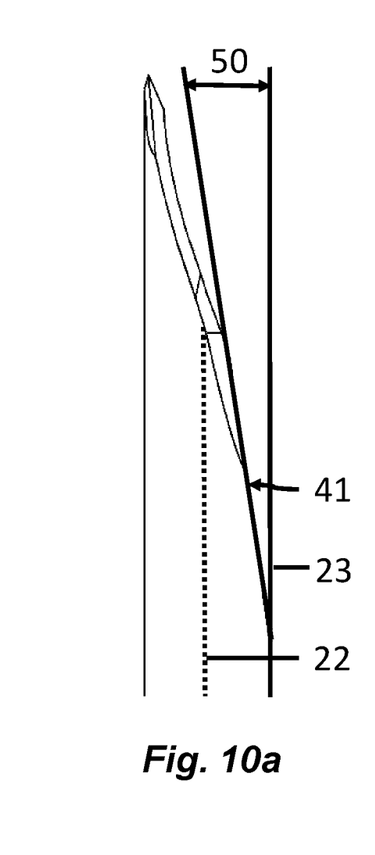
FIGS. 10a, 10b, 10c and 10d are side views of the proximal end of the multi-bevelled needle according to the third embodiment.
Figure 10B:
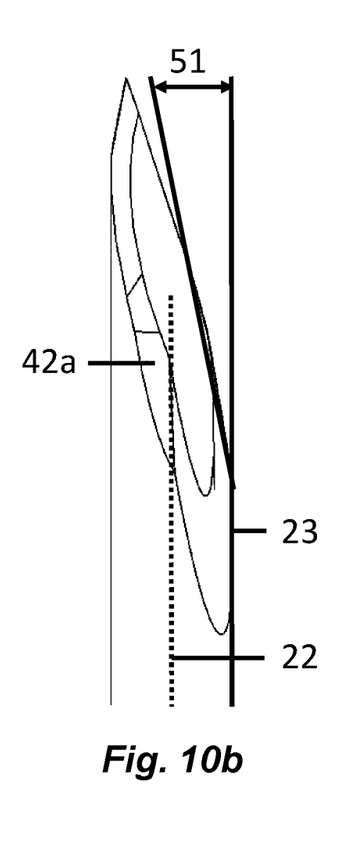
Figure 10C:
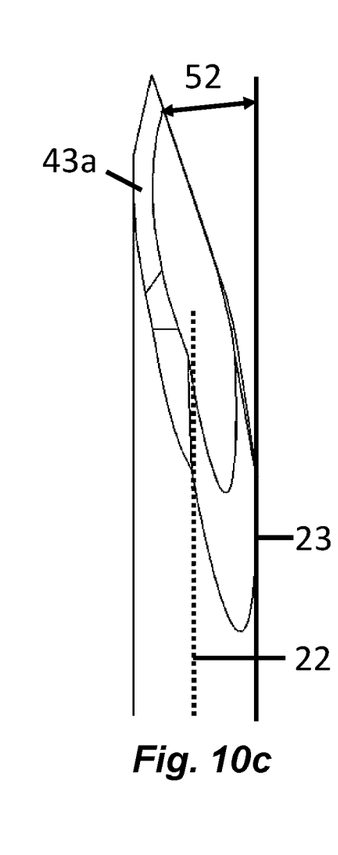
Figure 10D:
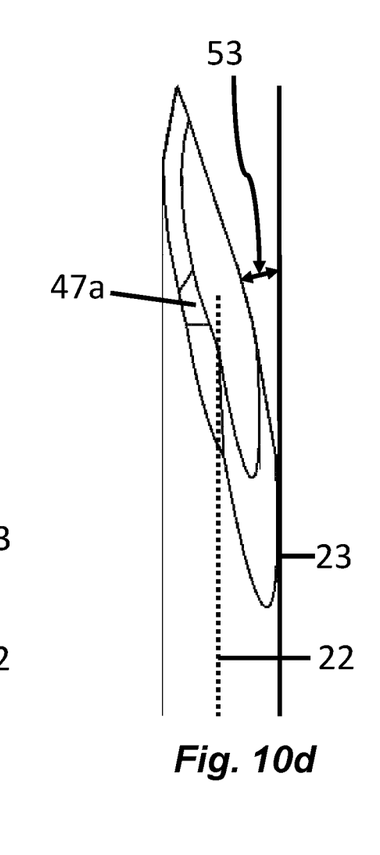

The first, second, and third inclination angles 50, 51, 52 of the third embodiment illustrated in FIGS. 8-10d are substantially identical to the first, second, and third inclination angles 50, 51, 52 of the second embodiment illustrated in FIG. 5-7. Similarly, the needle 10 of the third embodiment have the same first, second, and third rotation angles as those of the needle 10 of the second embodiment. On the other hand, as illustrated in FIG. 10d, the middle bevels 47a, 47b are formed or otherwise provided on the needle 10 by inclining the first reference plane 22 of the needle 10 at an angle 53 relative to the second reference plane 23 as well as by rotating the needle 10 about the first reference plane 22 at a fourth rotation angle with respect to the reference plane 22. This provides the middle bevels 47a, 47b with outwardly directed surfaces. In the embodiment illustrated in FIGS. 10d, the angle of inclination 53 is substantially 15° and the fourth rotation angle is substantially 35° (plus or minus 2° to account for tolerance), but are not limited thereto.

Figure 11A:
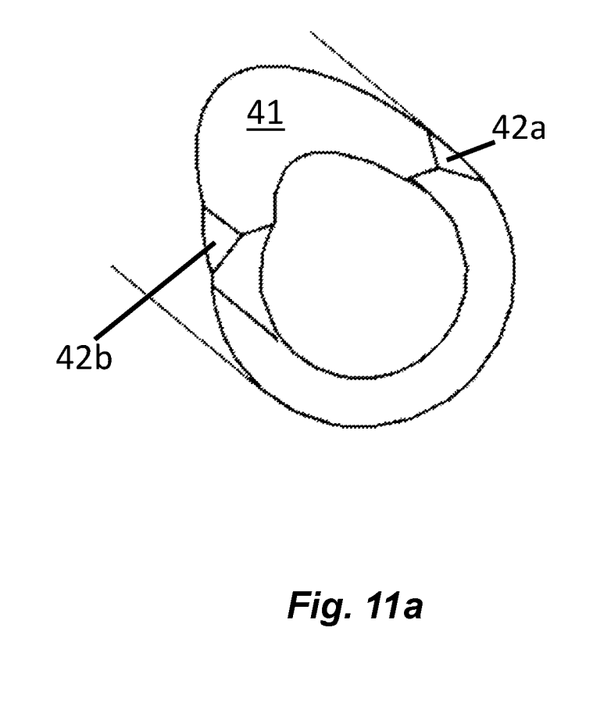
FIGS. 11a and 11b are cross-section views of the needle according to the second embodiment to illustrate a first peripheral angle.
Figure 11B:
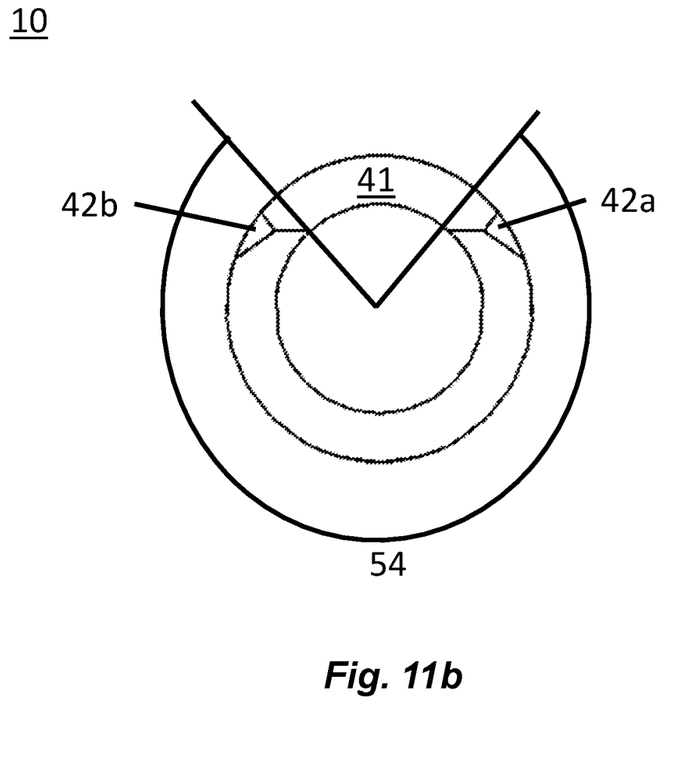
Figure 12A:
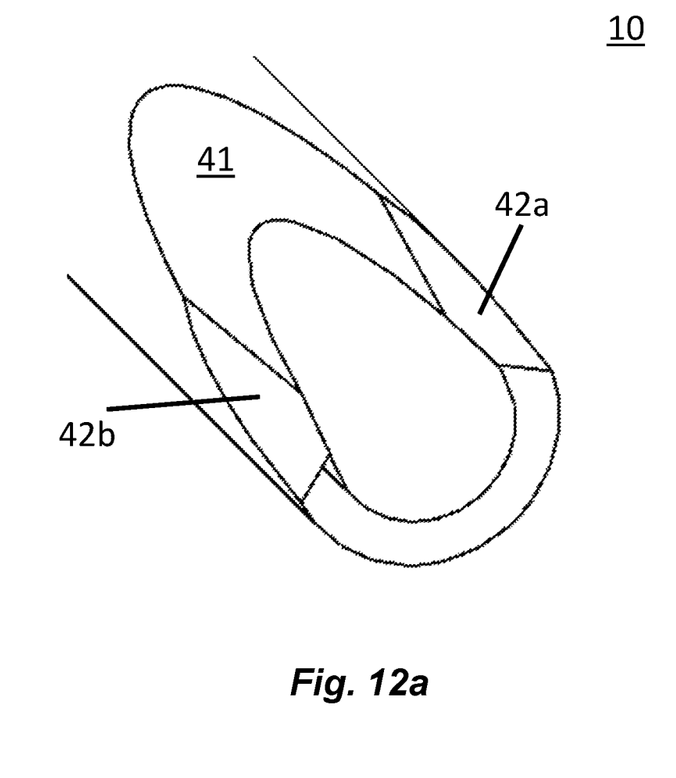
FIGS. 12a and 12b are cross-section views of the needle according to the second embodiment to illustrate a second peripheral angle.
Figure 12B:
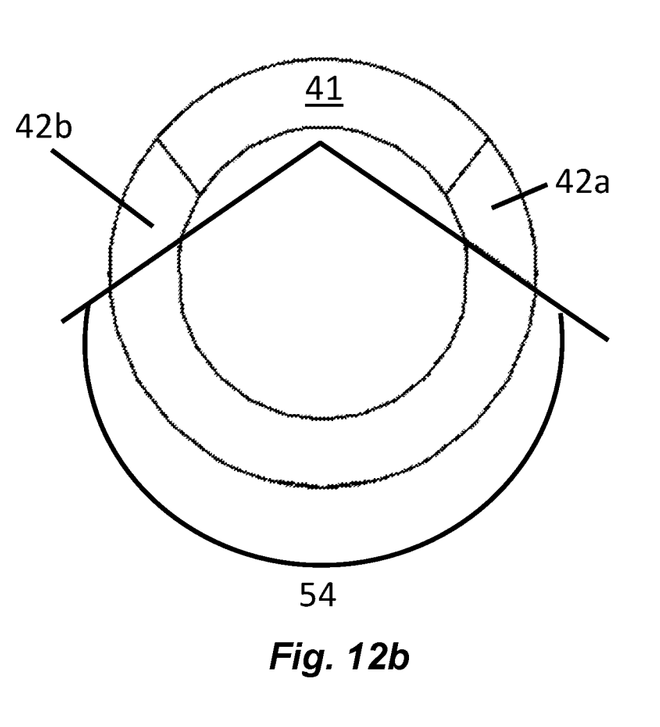
Figure 13A:
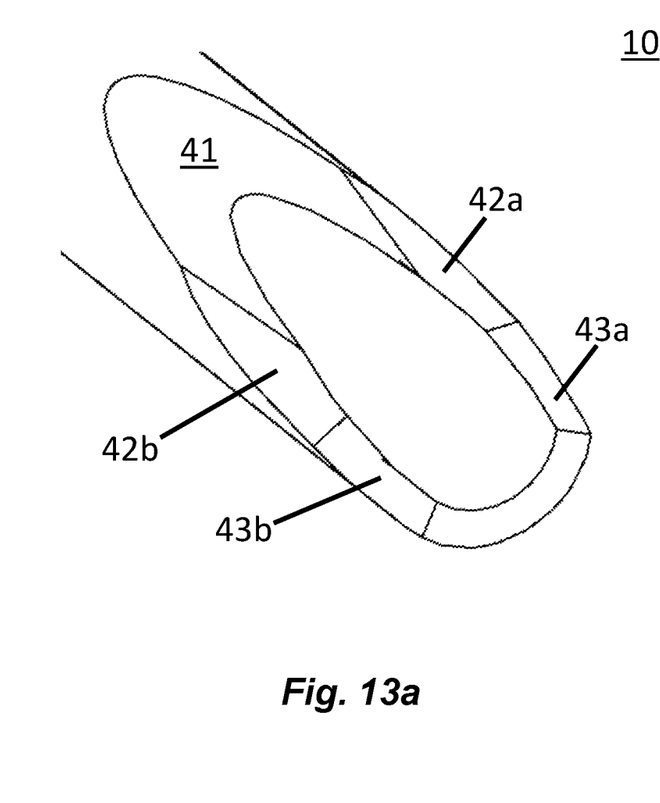
FIGS. 13a and 13b are cross-section views of the needle according to the second embodiment to illustrate a third peripheral angle.
Figure 13B:
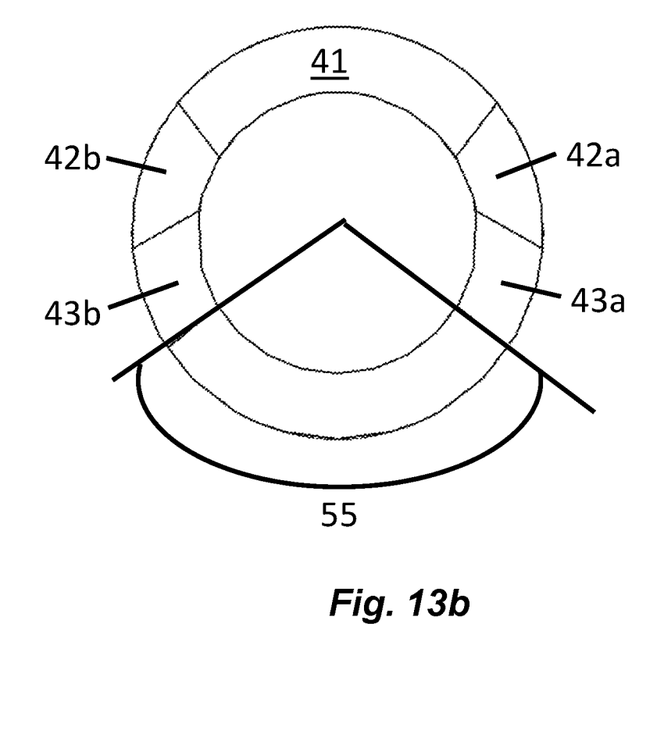

FIG. 11a-b are cross-section views created by cutting the needle 10 at the proximal end of the primary bevel. The cut is made in the middle of the intersection between the primary bevel 41 and the middle bevels 42a, 42b. As illustrated in FIG. 11b, the first peripheral angle 54 created by the cut is approximately 285°. FIG. 12a-b are cross-section views created by once more cutting the needle 10 at the proximal end of the primary bevel. The cut is made in the middle of the intersect 44a, 44b between the middle bevels 42a, 42b and the tip bevels 43a, 43b. As illustrated in FIG. 12b, the first peripheral angle 55 created by the cut is approximately 120°. FIG. 13a-b are cross-section views created by cutting the needle 10 in the middle of the tip bevels 43a, 43b. As illustrated in FIG. 13b, the first peripheral angle 55 created by the cut is approximately 100°.

Although the disclosure has been described in detail for the purpose of illustration based on what is currently considered to be the most practical and preferred embodiments, it is to be understood that such detail is solely for that purpose and that the disclosure is not limited to the disclosed embodiments but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A needle, comprising:
a needle body defining a first reference plane therethrough; and
a multi-bevelled point having a first face and a second face, wherein the point first face includes a primary bevel, two first middle bevels, two tip bevels, wherein each of the first middle bevels is located between the primary bevel and one of the tip bevels,
wherein the primary bevel is provided on the multi-bevelled point at a first angle of inclination and a first angle of rotation with respect to the first reference plane, the two first middle bevels are provided on the multi-bevelled point at a second angle of inclination and a second angle of rotation with respect to the first reference plane, the two tip bevels are provided on the multi-bevelled point at a third angle of inclination and a third angle of rotation with respect to the first reference plane,
wherein the second angle of rotation and the third angle of rotation are greater than the first angle of rotation respect to the first reference plane, and
wherein the second angle of rotation and the third angle of rotation are both outside a range of 30°-50°.

2. The needle of claim 1, wherein the second face includes a pair of back bevels, and wherein the second face is arranged 180 degrees from the first face.

3. The needle of claim 1, wherein the first angle of inclination is equal to or smaller than the second angle of inclination; and wherein the second angle of inclination is smaller than the third angle of inclination.

4. The needle of claim 1, wherein the second angle of rotation is different from the third angle of rotation.

5. The needle of claim 1, wherein the second angle of rotation and the third angle of rotation are equal to one another.

6. The needle of claim 1, wherein the first angle of rotation is 0°.

7. The needle of claim 1, wherein the multi-bevelled point has a first length measured from a proximal end of the tip bevels to a distal end of the primary bevel and a second length measured from a proximal end to the distal end of the primary bevel, the second length is greater than a half of the first length.

8. The needle of claim 1, wherein the needle has an inner diameter outside a range between 0.0075"-0.0090" (0.1905 mm -0.2286 mm).

9. The needle of claim 1, wherein the needle has an outer diameter outside a range between 0.0130"-0.0135" (0.3302 mm -0.3429 mm).

10. The needle of claim 1, wherein the first face and the second face are located on two opposite ends of the multi-bevelled point.

11. The needle of claim 1, wherein the multi-beveled point further includes two second middle bevels located on the first face, each of the second middle bevels is located between the primary bevel and one of the tip bevels, the two second middle bevels are provided on the needle at a fifth angle of inclination and a fifth angle of rotation with respect to the first reference plane.

12. The needle of claim 11, wherein the first angle of inclination is equal or smaller than the fifth angle of inclination.

13. The needle of claim 12, wherein the second angle of rotation is smaller than the fifth angle of rotation.

14. A needle, comprising:
a needle body defining a first reference plane therethrough; and
a multi-bevelled point having a first face and a second face, wherein the first face includes a primary bevel, two first middle bevels, two tip bevels, wherein the second face includes a pair of back bevels,
wherein the primary bevel is provided on the first face at a first angle of inclination and a first angle of rotation with respect to the first reference plane, wherein the two first middle bevels are provided on the first face at a second angle of inclination and a second angle of rotation with respect to the first reference plane,
wherein the second angle of rotation is greater than the first angle of rotation respect to the first reference plane, and
wherein the second angle of rotation is outside a range of 30°-50°.

15. The needle of claim 14, wherein each of the first middle bevels are located between the primary bevel and one of the tip bevels.

16. The needle of claim 14, wherein the second face is arranged 180 degrees from the first face.

17. The needle of claim 14, wherein the first angle of inclination is equal to or smaller than the second angle of inclination.

18. The needle of claim 14, wherein the two tip bevels are provided on the first face at a third angle of inclination and a third angle of rotation with respect to the first reference plane.

* * * * *